(12) United States Patent
Teigman et al.

(10) Patent No.: US 6,506,157 B1
(45) Date of Patent: Jan. 14, 2003

(54) DUAL DOPPLER ARTERY LIGATION AND HEMORRHOID TREATMENT SYSTEM

(76) Inventors: Jack Teigman, 120 1st St. E., #105, St. Petersburg, FL (US) 33715; John M. D'Angelo, 6510 1st Ave. S., St. Petersburg, FL (US) 33710

( * ) Notice: Subject to any disclaimer, the term of this patent is extended or adjusted under 35 U.S.C. 154(b) by 0 days.

(21) Appl. No.: 09/946,191

(22) Filed: Sep. 5, 2001

(51) Int. Cl.[7] .................................................. A61B 8/06
(52) U.S. Cl. ...................................... 600/439; 600/453
(58) Field of Search ................................. 600/101, 103, 600/160, 184, 437, 439, 453

(56) References Cited

U.S. PATENT DOCUMENTS 5,570,692 A * 11/1996 Morinaga ................... 600/453
6,014,589 A * 6/2000 Farley et al. ................. 607/98

* cited by examiner

Primary Examiner—Francis J. Jaworski

(57) ABSTRACT

A dual Doppler artery ligation and hemorrhoid treatment system has a probe. The probe has a disposable cylinder with a cone-shaped cap at the distal end and a support adjacent to the proximal end. A series of white light emitting diodes is mounted within the support. The support has a backing plate proximally and an opening to the cylinder and cone distally. The cylinder has an opening adjacent to its distal end and a pair of ultrasonic transducers secured on the cylinder laterally spaced on the center line proximal side of the opening. An echo analyzer is operatively coupled to the probe and is adapted to emit signals and to detect and analyze received signals as a function of the blood flow there adjacent to produce an output which varies as a function of the arterial blood flow of a hemorrhoid extending through the aperture.

7 Claims, 5 Drawing Sheets

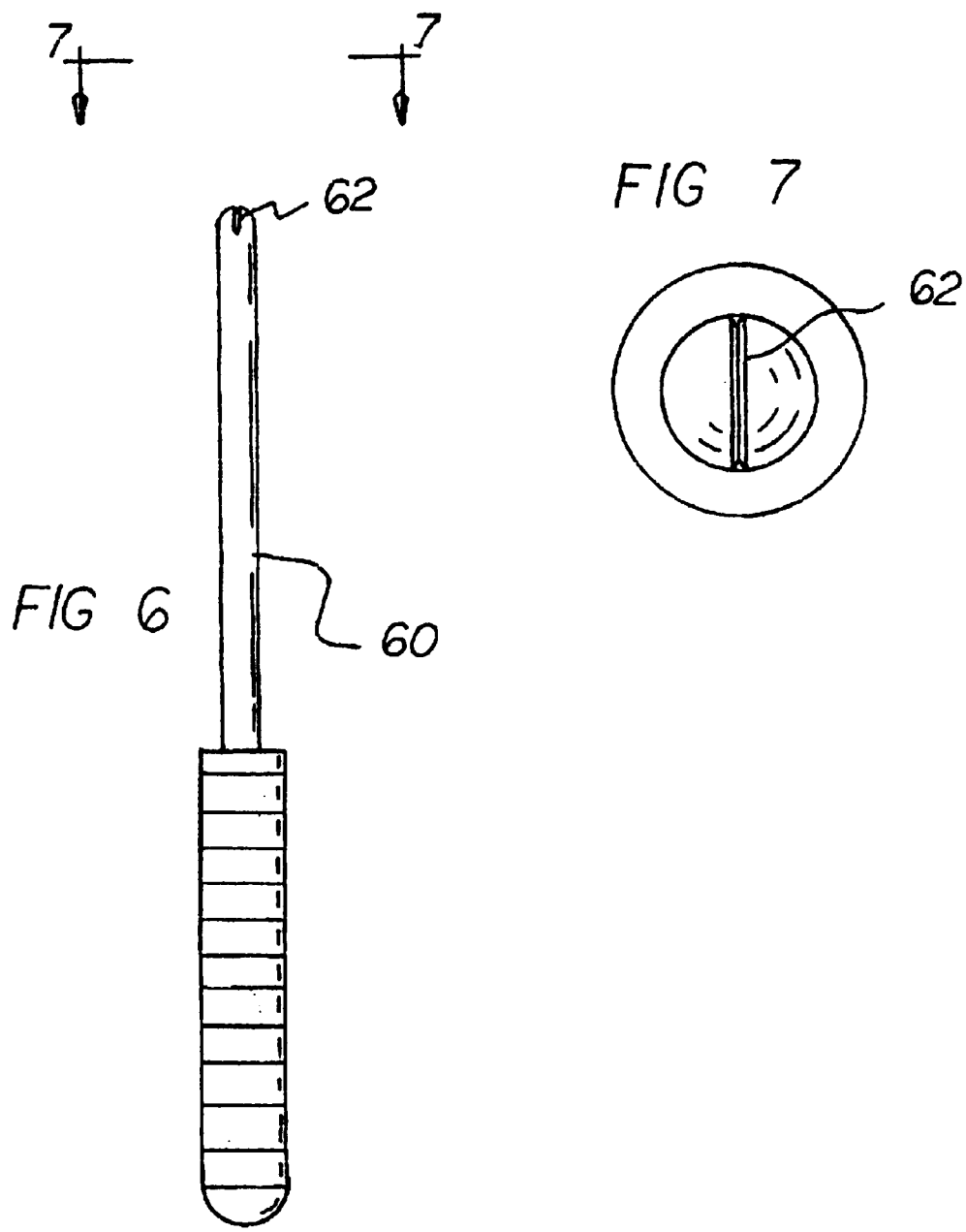

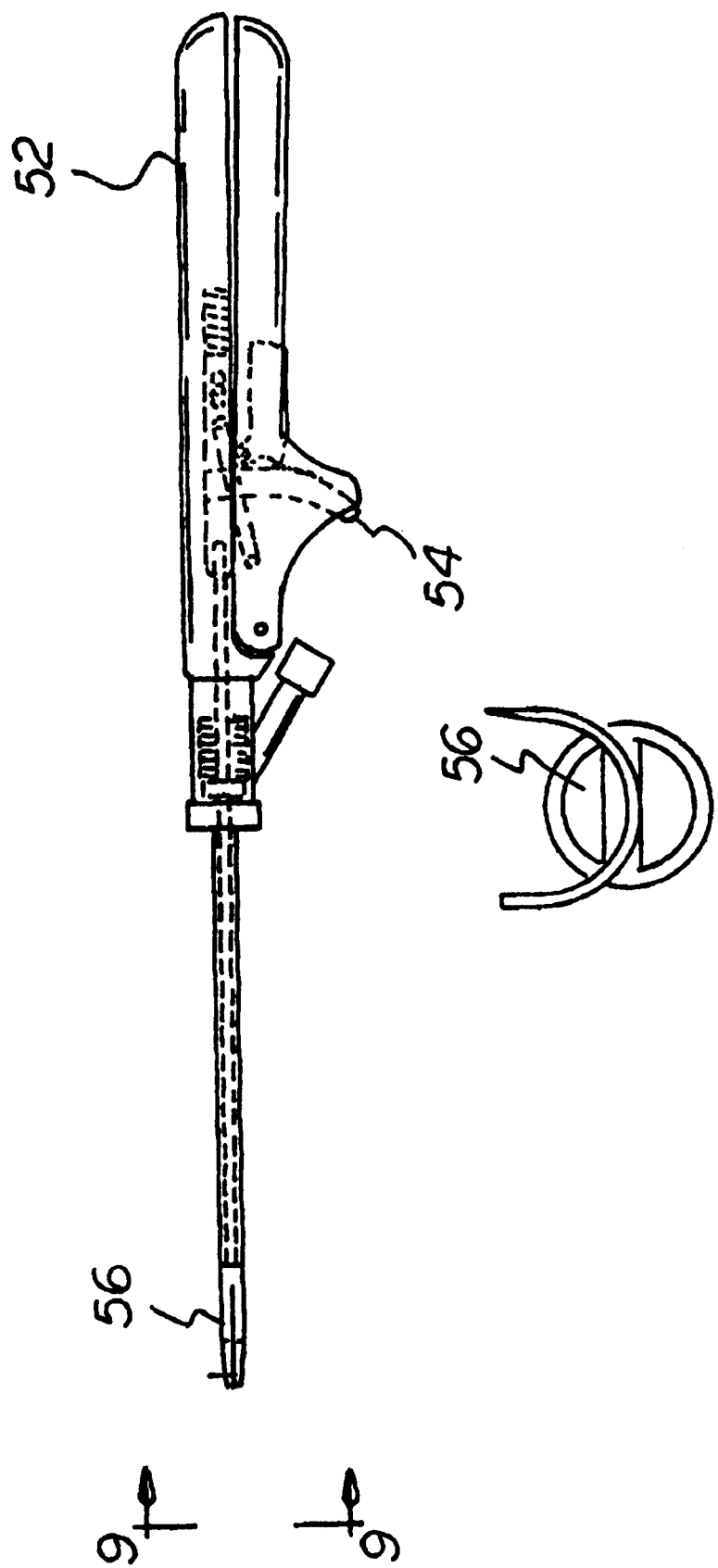

DUAL DOPPLER ARTERY LIGATION AND HEMORRHOID TREATMENT SYSTEM

BACKGROUND OF THE INVENTION

1. Field of the Invention

The present invention relates to a dual Doppler artery ligation and hemorrhoid treatment system and more particularly pertains to locating, ligating and reducing hemorrhoids in an accurate and convenient manner.

2. Description of the Prior Art

The use of devices of known designs and configurations for locating hemorrhoids and for removing them is known in the prior art. More specifically, devices of known designs and configurations for locating hemorrhoids and for removing them previously devised and utilized for the purpose of locating and removing hemorrhoids through conventional methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,570,692 to Morinaga discloses an ultrasonic Doppler blood flow detector for hemorrhoid artery ligation. Also, U.S. Pat. No. 5,413,583 to Wohlers discloses a force limiting arrangement for needle holder for endoscopic surgery.

While these devices fulfill their respective, particular objectives and requirements, the aforementioned patents do not describe a dual Doppler artery ligation and hemorrhoid treatment system that allows locating, ligating and reducing hemorrhoids in an accurate and convenient manner.

In this respect, the dual Doppler artery ligation and hemorrhoid treatment system according to the present invention substantially departs from the conventional concepts and designs of the prior art, and in doing so provides an apparatus primarily developed for the purpose of locating, ligating and treatment hemorrhoids in an accurate and convenient manner.

Therefore, it can be appreciated that there exists a continuing need for a new and improved dual Doppler artery ligation and hemorrhoid treatment system which can be used for locating, ligating and treatment hemorrhoids in an accurate and convenient manner. In this regard, the present invention substantially fulfills this need.

SUMMARY OF THE INVENTION

In view of the foregoing disadvantages inherent in the known types of devices of known designs and configurations for locating hemorrhoids and for removing them now present in the prior art, the present invention provides an improved dual Doppler artery ligation and hemorrhoid treatment system. As such, the general purpose of the present invention, which will be described subsequently in greater detail, is to provide a new and improved dual Doppler artery ligation and hemorrhoid treatment system and method which has all the advantages of the prior art and none of the disadvantages.

To attain this, the present invention essentially comprises a suitcase. The suitcase has a foam interior lining. The suitcase also has a plurality of discrete areas for the receipt of components adapted for use in hemorrhoidal surgery. Next provided is a probe. The probe has a transparent disposable cylinder. The cylinder has a distal end and a proximal end. The probe also has a cone-shaped cap at the distal end. The probe also has a short opaque cylindrical support with an enlarged diameter adjacent to the proximal end. A series of light emitting diodes in a generally circular shape is provided. The light source is mounted within the support. The support has an opaque backing plate proximally. The support also has an opening to the cylinder and cone distally. A light emitting diode is provided on the backing plate. The probe also has a frusto-conical connector between the cylinder and the support. The disposable cylinder has a laterally tapered circumferential opening of about 60 degrees, about 1 inch circumferentially and about ¼ inch axially adjacent to the distal end of the aperture. A pair of ultrasonic 8 MHz transducers are provided. The transducers are secured within the cylinder laterally spaced from each other between about ⅛ inch and ¼ inch circumferentially on the proximal side of the opening. The transducers detect hemorrhoid arterial flow in adjacent areas of a patient. The focal point is directly below the distal end aperture. It is ¾ inch below the outside wall of the probe. This provides more specific information to the system for arterial localization. The dual transducers markedly reduce extraneous signals from non-pertinent arteries and enhance the sensitivity of the hemorrhoid reduction system. A handle is provided. The handle depends proximally at an obtuse angle from the support. This prevents mechanical interference with the patient support table. An electrical connector is provided. The electrical connector extends through the handle for powering the LED's. A plurality of supplemental cylinders and a plurality of supplemental cones are provided. Next, an echo analyzer is provided. The echo analyzer is operatively coupled by supplemental wires to the probe. The supplemental wires extend through the handle. The analyzer is adapted to emit signals and to detect and analyze received signals through a double Doppler effect as a function of the blood flow adjacent to the opening. The analyzer is further adapted to produce an audio output which varies as a function of the arterial blood flow of a hemorrhoid extending through the aperture. Additionally, the analyzer is adapted to produce a flashing visual output through the red light emitting diode which also varies as a function of the arterial blood flow of a hemorrhoid extending through the aperture. Monaural earphones are provided. The earphones are adapted to be worn by a surgeon. The earphones are operatively coupled to the analyzer. In this manner, the surgeon may move the probe in response to the sound of a weakly detected signal to insure that the probe is properly positioned so that a hemorrhoid may be positioned through the aperture for being ligated and removed. The earphones are unilateral to allow auditory access to the patient environment. Next provided is a transformer. The transformer is adapted to be coupled between a source of alternating current and the analyzer for the electrical powering of the analyzer, probe, white and red light emitting diodes. A plurality of needle holders are provided. Each needle holder has a proximal end with a gripping region ergonomically similar to a screwdriver handle. Each needle holder also has a trigger adapted to be manipulated by a surgeon. Each needle holder further has a distal end for supporting a needle with sutures. The sutures are specifically adapted to be passed through a hemorrhoid extending through the aperture in the cylinder for ligation and removal. Further, a plurality of knot pushers are provided. Each knot pusher is in the form of an elongated rod with a crossing V-shaped recess at one end and one ergonomically designed handle grip end. The knot pushers function to advance a knot in a suture passing around the hemorrhoid artery.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved dual Doppler artery ligation and hemorrhoid treatment system which has all of the advantages of the prior art devices of known designs and configurations for locating hemorrhoids and for removing them and none of the disadvantages.

It is another object of the present invention to provide a new and improved dual Doppler artery ligation and hemorrhoid treatment system which may be easily and efficiently manufactured and marketed.

It is further object of the present invention to provide a new and improved dual Doppler artery ligation and hemorrhoid treatment system which is of durable and reliable constructions.

An even further object of the present invention is to provide a new and improved dual Doppler artery ligation and hemorrhoid treatment system which is susceptible of a low cost of manufacture with regard to both materials and labor, and which accordingly is then susceptible of low prices of sale to the consuming public, thereby making such dual Doppler artery ligation and hemorrhoid treatment system economically available to the buying public.

Even still another object of the present invention is to provide a dual Doppler artery ligation and hemorrhoid treatment system for locating, ligating and treatment hemorrhoids in an accurate and convenient manner.

Lastly, it is an object of the present invention to provide a new and improved dual Doppler artery ligation and hemorrhoid treatment system having a probe. The probe has a disposable cylinder with a cone-shaped cap at the distal end and a support adjacent to the proximal end. A white light emitting diode is mounted within the support. The support has a backing plate proximally and an opening to the cylinder and cone distally. The cylinder has an opening adjacent to its distal end and a pair of ultrasonic transducers secured on the cylinder laterally spaced on the proximal side of the opening. An echo analyzer is operatively coupled to the probe and is adapted to emit signals and to detect and analyze received signals as a function of the blood flow there adjacent to produce an output which varies as a function of the arterial blood flow of a hemorrhoid extending through the aperture.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a front elevational view of the knot pusher shown in FIG. 1.

FIG. 7 is a top elevational view of the knot pusher shown taken along line 7—7 of FIG. 6.

FIG. 8 is a side elevational view of the needle holder shown in FIG. 1.

FIG. 9 is a front elevational view of the needle holder taken along line 9—9 of FIG. 8.

The same reference numerals refer to the same parts throughout the various Figures.

DESCRIPTION OF THE PREFERRED EMBODIMENT

Figure 1:
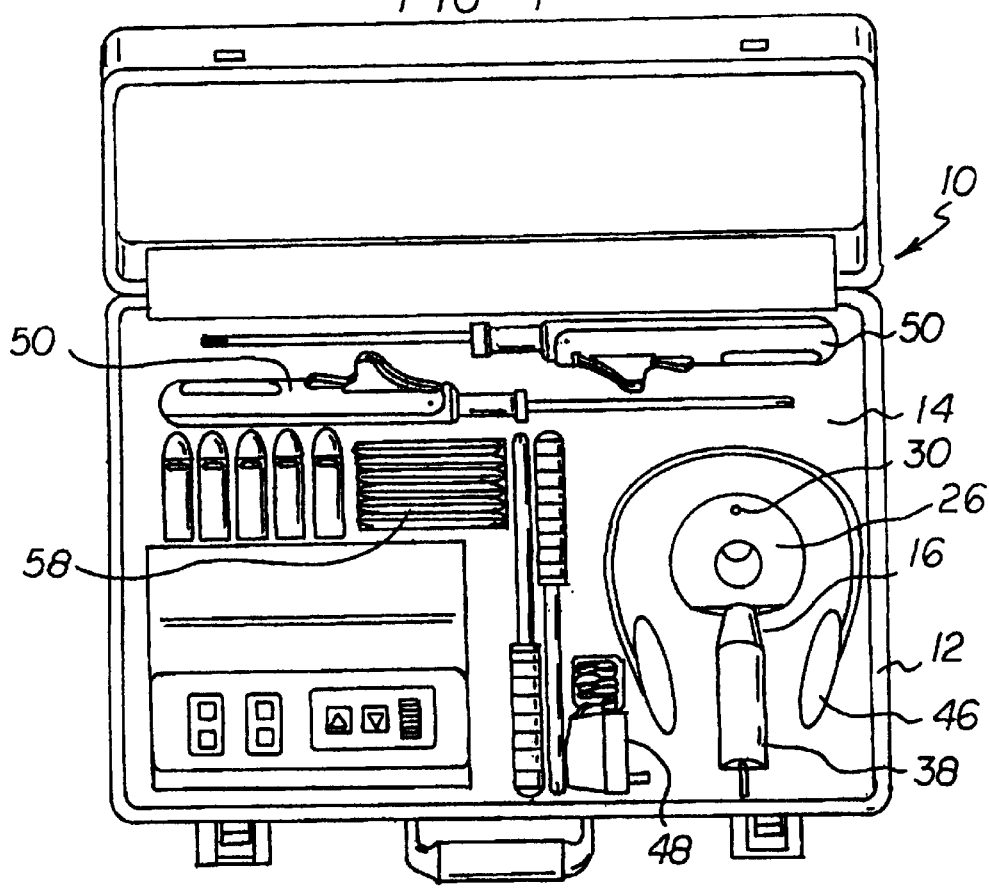
FIG. 1 is an elevational view of a hemorrhoid ligation system constructed in accordance with the principles of the present invention.

With reference now to the drawings, and in particular to FIG. 1 thereof, the preferred embodiment of the new and improved dual Doppler artery ligation and hemorrhoid treatment system embodying the principles and concepts of the present invention and generally designated by the reference numeral 10 will be described.

The present invention, the dual Doppler artery ligation and hemorrhoid treatment system 10 is comprised of a plurality of components. Such components in their broadest context include a a probe and an echo analyzer. Such components are individually configured and correlated with respect to each other so as to attain the desired objective.

First provided is a suitcase 12. The suitcase has a foam interior lining 14. The suitcase also has a plurality of discrete areas for the receipt of components adapted for use in hemorrhoidal surgery. Note FIG. 1. In the preferred embodiment, the suitcase is about 1.5 feet by 2 feet by 0.5 feet deep.

Figure 2:
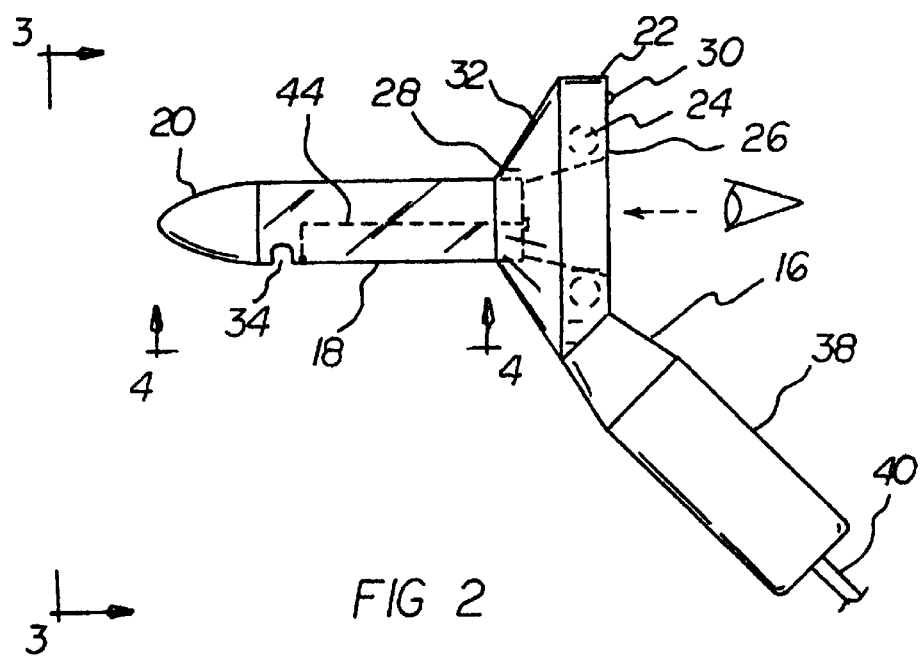
FIG. 2 is a side elevational view of the probe shown in FIG. 1.
Figure 3:
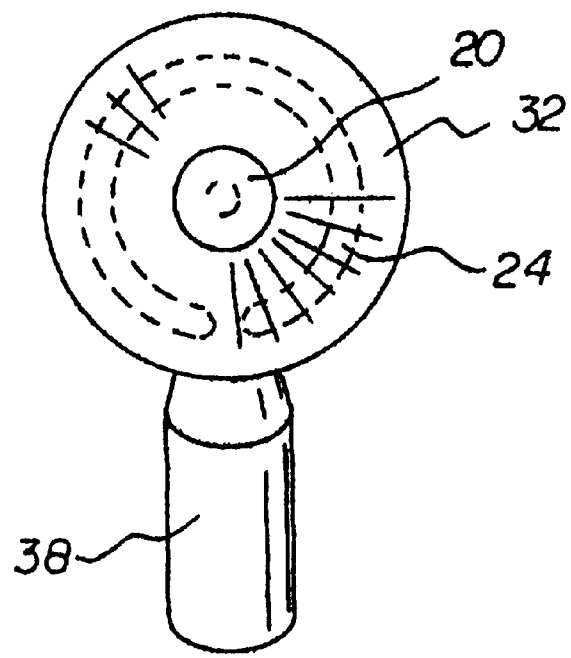
FIG. 3 is a front elevational view of the probe shown in FIG. 2 taken along line 3—3 of FIG. 2.
Figure 5:
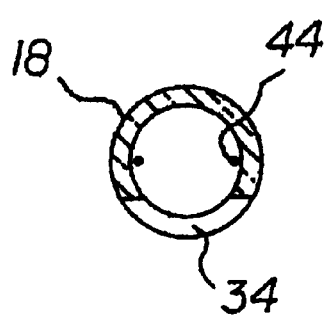
FIG. 5 is a cross sectional view of the probe taken along line 5—5 of FIG. 4.
Figure 4:
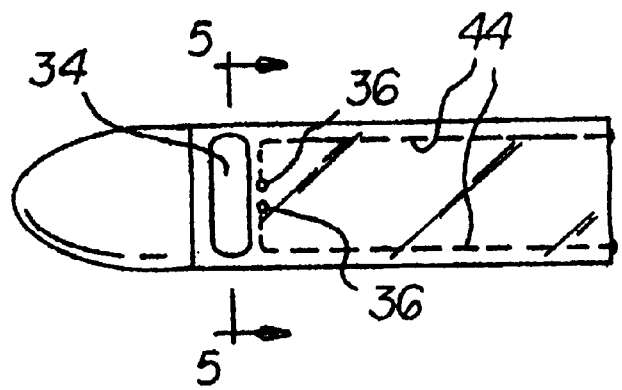
FIG. 4 is a bottom elevational view of the probe shown in FIG. 2 taken along line 4—4 of FIG. 2.
Figure 10:
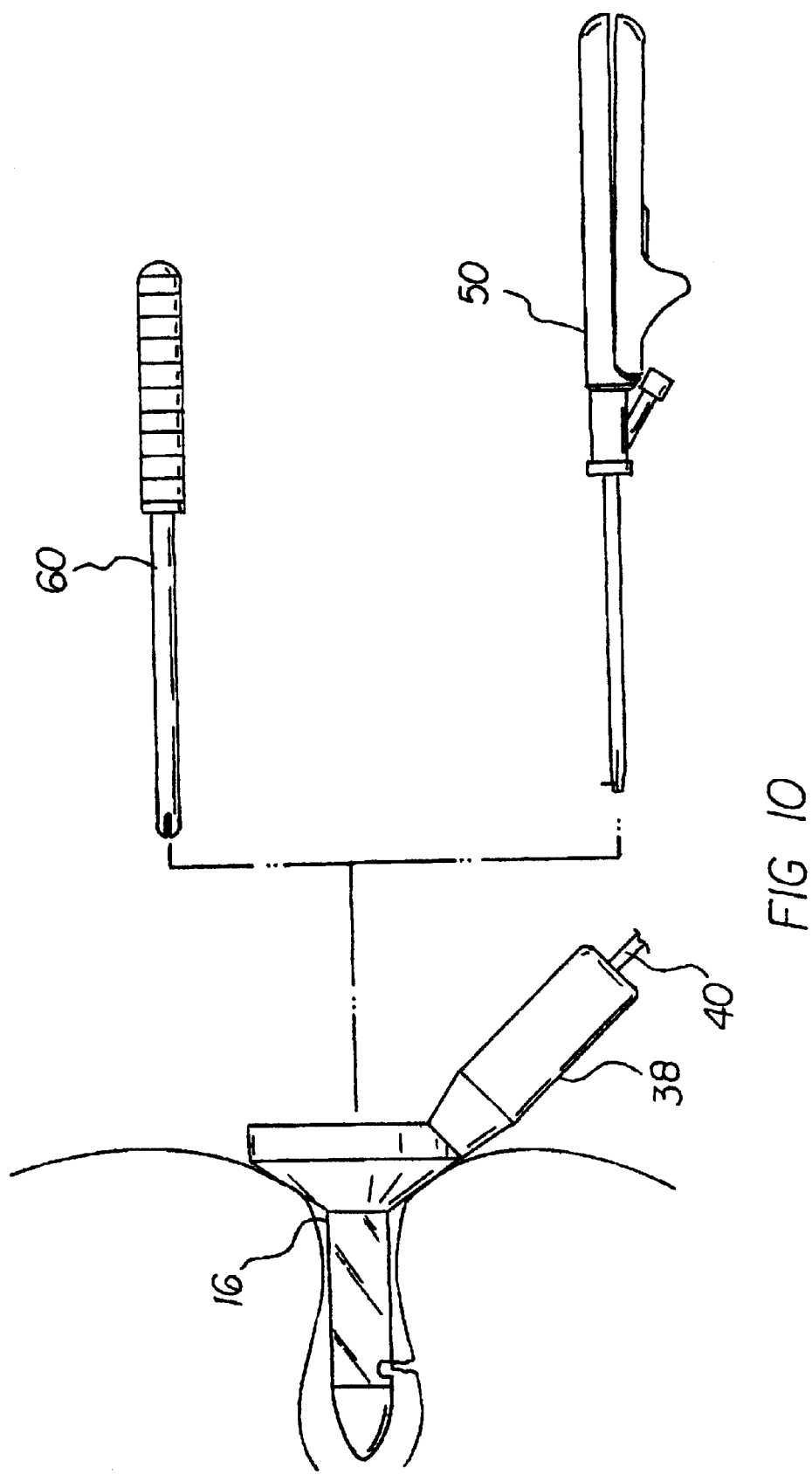
FIG. 10 is a side elevational view of the probe shown in FIGS. 2 in operative position and in association with the knot pusher of FIG. 6 and the needle holder of FIG. 8.

Next provided is a probe 16. Note FIGS. 2 and 3. The probe has a transparent disposable cylinder 18. The cylinder has a distal end and a proximal end. The probe also has a cone-shaped cap 20 at the distal end. The probe also has a short opaque cylindrical support 22 with an enlarged diameter adjacent to the proximal end. White light diodes 24 in a generally circular shape is provided. The support has an opaque backing plate 26 proximally. The support also has an opening 28 to the cylinder and cone distally. A red light emitting diode 30 is provided on the backing plate. The probe also has a frusto-conical connector 32 between the cylinder and the support. The cylinder has a tapered circumferential opening 34 of about 60 degrees, about 1 inch circumferentially and about ¼ inch axially adjacent to the distal end of the aperture. A pair of ultrasonic transducers 36 are provided. The transducers are secured on the interior of the cylinder laterally spaced from each other between about ⅛ inch and ¼ inch circumferentially on the proximal side of the opening. They are focused in the middle of the aperture ¾ inch below the cylinder surface. The transducers detect hemorrhoid arterial flow in adjacent areas of a patient. A handle 38 is provided. The handle depends proximally at an obtuse angle from the support. An electrical connector 40 is provided. The electrical connector extends through the handle for powering the LED's. Although only one probe is shown in the suitcase of FIG. 1, two more could readily be provided as part of the system.

A plurality of supplemental cylinders and a plurality of supplemental cones are provided. Reference is made again to FIG. 1.

Next, an echo analyzer 42 is provided. The echo analyzer is operatively coupled by supplemental wires 44 to the probe. The supplemental wires extend through the handle. The analyzer is adapted to emit signals and to detect and analyze received signals through a double Doppler effect as a function of the blood flow adjacent to the opening. The analyzer is further adapted to produce an audio output which varies as a function of the arterial blood flow of a hemorrhoid extending through the aperture. Additionally, the analyzer is adapted to produce a flashing visual output through the light emitting diode which also varies as a function of the arterial blood flow of a hemorrhoid extending through the aperture. The analyzer is a box, which on its front face has on the left, a power "on" and a power "off" touch pad. There adjacent are a light source "on" and "off" touch pad. Also provided is a volume "up" and "down" touch pad with an associated graphic display between "max" and "min". Lastly there is a small light to indicate that audio is on. The echo analyzer is about 10 inches by 10 inches by 3 inches high.

Monaural earphones 46 are provided. The earphones are adapted to be worn by a surgeon. The earphones are operatively coupled to the analyzer. In this manner, the surgeon may move the probe in response to the sound of a weakly detected signal to insure that the probe is properly positioned so that a hemorrhoid may be positioned through the aperture for being ligated and removed.

Next provided is a transformer 48. The transformer is adapted to be coupled between a source of alternating current and the analyzer for the electrical powering of the analyzer, probe, light emitting diode and bulb. The probe and analyzer are an improvement over the single Doppler system described in U.S. Pat. No. 5,570,692, previously discussed, the subject matter of which is incorporated herein by reference. As an alternate embodiment, the system could be battery powered.

A plurality of needle holders 50 are provided. Each needle holder has a proximal end with a gripping region 52. Each needle holder also has a trigger 54 adapted to be manipulated by a surgeon. Each needle holder further has a distal end 56 for supporting a needle with sutures. The sutures are adapted to be passed around a hemorrhoid artery extending through the aperture in the cylinder for ligation and treatment. The needle holder is a miniaturized version of that described in U.S. Pat. No. 5,413,583, previously described, the subject matter of which is incorporated herein by reference. The needle holders are about 12 inches long.

A plurality of packets 58 of Ethicon UR-6 needles with 2.0 Vicryl is provided for initial use.

Further, a plurality of knot pushers 60 are provided. Each knot pusher is in the form of an elongated rod with a crossing V-shaped recess 62 at one end. The knot pushers function to advance a knot in a suture passing through the hemorrhoid.

The present invention, with its pair of mutually spaced ultrasonic transducers, in combination with the probe, disposable cylinder, LED's, and echo analyzer is designed for increased safety, visibility, simplicity of use, and easy cleaning. The invention is dependable and ergonomic with reusable cold light source and with a maximal arterial LED indicator. The disposable Doppler cylinders feature twin transducer technology for enhanced arterial location and lessened false signals. It also includes titanium needle holders for ultimate control, visibility, safety, and durability. Lastly, it includes a wide range of useful accessories included as part of the system.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dual Doppler artery ligation and hemorrhoid treatment system for locating and ligating hemorroidal arteries and treating hemorrhoids in an accurate, safe, and convenient manner comprising, in combination:

a suitcase with a foam interior lining and having a plurality of discrete areas for the receipt of components adapted for use in hemorrhoidal surgery;

a probe having a transparent cylinder with a distal end and a proximal end, the probe also having a cone-shaped cap at the distal end and a short opaque cylindrical support with an enlarged diameter adjacent to the proximal end, a white light emitting diode having a generally circular shape mounted within the support, the support having an opaque backing plate proximally and an opening to the cylinder and cone distally, a red light emitting diode on the backing plate, the probe also having a frusto-conical connector between the cylinder and the support, the disposable cylinder having a circumferential opening of about 60 degrees, about 1 inch circumferentially and about ¼ inch axially adjacent to the distal end of the aperture, a pair of ultrasonic transducers secured within the cylinder laterally spaced from each other between about ⅛ inch and ¼ inch circumferentially on the proximal side of the opening for detecting hemorrhoid arterial flow in adjacent areas of a patient, a handle depending proximally at an obtuse angle from the support with an electrical connector extending through the handle for powering the LED's;

a plurality of supplemental cylinders and a plurality of supplemental cones;

an echo analyzer operatively coupled by supplemental wires to the probe, the supplemental wires extending through the handle, the analyzer adapted to emit signals and to detect and analyze received signals through a double Doppler effect as a function of the blood flow adjacent to the opening and to produce an audio output which varies as a function of the arterial blood flow of a hemorrhoid extending through the aperture, the analyzer also adapted to produce a flashing visual output through the light emitting diode which also varies as a function of the arterial blood flow of a hemorrhoid extending through the aperture;

monaural earphones adapted to be worn by a surgeon, the earphones being operatively coupled to the analyzer whereby the surgeon may move the probe in response to the sound of a weakly detected signal to insure that the probe is properly positioned so that a hemorrhoid artery may be positioned beneath the aperture for being ligated thus treating the hemorrhoid;

a transformer adapted to be coupled between a source of alternating current and the analyzer for the electrical powering of the analyzer, probe and light emitting diodes;

a plurality of needle holders, each needle holder having a proximal end with a gripping region and a trigger adapted to be manipulated by a surgeon and a distal end for supporting a needle with sutures adapted to be passed through a hemorrhoid extending through the aperture in the cylinder for ligation and removal;

a plurality of packets of specific sutures for hemorrhoidal artery ligation; and a plurality of knot pushers, each knot pusher being in the form of an elongated rod with a V-shaped recess at one end for advancing a knot in a suture passing through the hemorrhoid.

2. A dual Doppler artery ligation and hemorrhoid treatment system comprising:

a probe having a cylinder with a cone-shaped cap at the distal end and with a support adjacent to the proximal end, a white light emitting diode mounted within the support, the support having a backing plate proximally and an opening to the cylinder and cone distally, the cylinder having an opening adjacent to its distal end and a pair of ultrasonic transducers secured on the cylinder laterally spaced on the midline proximal side of the opening; and an echo analyzer operatively coupled to the probe adapted to emit signals and to detect and analyze received signals as a function of the blood flow there adjacent to produce an output which varies as a function of the arterial blood flow of a hemorrhoid extending adjacent to the aperture.

3. The system as set forth in claim 2 and further including earphones adapted to be worn by a surgeon, the monaural earphones being operatively coupled to the analyzer whereby the surgeon may move the probe in response to the sound of weakly detected signals to insure that the probe is properly positioned whereby a hemorrhoid artery may be positioned adjacent to the aperture for being ligated and treated.

4. The system as set forth in claim 2 and further including a transformer adapted to be coupled to a source of alternating current and to the analyzer for the electrical powering of the analyzer, probe, and bulb.

5. The system as set forth in claim 2 wherein the system is battery powered.

6. The system as set forth in claim 2 and further including a needle holder having a proximal end with a screwdriver type gripping region and a trigger adapted to be manipulated by a surgeon and a distal end for supporting a needle with sutures adapted to be passed through a hemorrhoid extending through the aperture in the cylinder for ligation and removal.

7. The system as set forth in claim 2 and further including a knot pusher being in the form of an elongated rod with a V-shaped recess at one end for advancing a knot in the suture passing through the hemorrhoid.

* * * * *